United States Patent [19]

Restaino

[11] 4,049,731
[45] Sept. 20, 1977

[54] STABILIZED POLYMERIZABLE COMPOSITIONS

[75] Inventor: Alfred Joseph Restaino, Wilmington, Del.

[73] Assignee: ICI United States Inc., Wilmington, Del.

[21] Appl. No.: 595,412

[22] Filed: July 14, 1975

[51] Int. Cl.² .................... C10G 9/16; C08K 5/13
[52] U.S. Cl. .................... 260/666.5; 208/48 AA; 252/182; 260/45.95 R; 260/465.9; 260/619 R; 260/620; 260/859 R; 260/861; 560/1; 560/205
[58] Field of Search ........... 260/666.5, 669 R, 669 A, 260/45.95, 619 R, 620, 486 R, 468 R, 468 L, 465.9; 252/182

[56] References Cited

U.S. PATENT DOCUMENTS

| | | | |
|---|---|---|---|
| 2,249,793 | 7/1941 | Soday | 260/669 A |
| 2,304,466 | 8/1942 | Matheson et al. | 260/45.95 R |
| 2,479,948 | 8/1949 | Luten et al. | 44/78 |
| 2,697,111 | 12/1954 | Bell et al. | 260/45.95 G |
| 2,785,188 | 3/1957 | Coe | 260/396 |
| 3,153,098 | 10/1964 | Boag | 260/620 |
| 3,251,801 | 5/1966 | Boag | 260/45.95 |
| 3,812,193 | 5/1974 | Randell et al. | 260/620 |
| 3,959,358 | 5/1976 | Jursich | 260/486 R |

FOREIGN PATENT DOCUMENTS

| | | | |
|---|---|---|---|
| 66,455 | 9/1950 | Netherlands | 44/78 |

OTHER PUBLICATIONS

"Stabilized Cracked Gasoline" C.A.44, 11079f Bataafsche (Neth. 66,455 Sept. 15, 1950).

*Primary Examiner*—Delbert E. Gantz
*Assistant Examiner*—G. E. Schmitkons

[57] ABSTRACT

Compositions stabilized against premature polymerization are disclosed. These compositions contain
a. a vinyl or vinylidene monomer capable of free radical polymerization, and
b. a polymerization inhibitor having the following general formula:

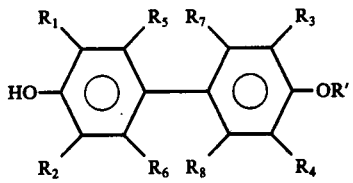

wherein
R' is hydrogen or an alkyl group containing from 1 to 4 carbon atoms,
$R_1$, $R_2$, $R_3$ and $R_4$ are alkyl groups containing from 1 to 5 carbon atoms, and
$R_5$, $R_6$, $R_7$ and $R_8$ are hydrogen or alkyl groups containing from 1 to 5 carbon atoms provided that only two of these may be a secondary or a tertiary alkyl group.

9 Claims, No Drawings

STABILIZED POLYMERIZABLE COMPOSITIONS

BACKGROUND OF THE INVENTION

1. Field of the Invention

The present invention relates generally to liquid, polymerizable vinyl or vinylidene monomer containing compositions stabilized against premature polymerization. More particularly, the invention relates to a composition containing a vinyl or vinylidene monomer capable of free radical polymerization and a biphenol derivative having the following general formula:

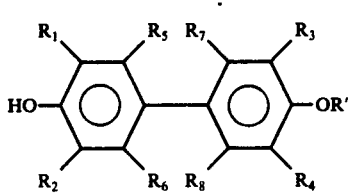

wherein
- R' is hydrogen or an alkyl group containing from 1 to 4 carbon atoms,
- $R_1$, $R_2$, $R_3$ and $R_4$ are alkyl groups containing from 1 to 5 carbon atoms, and
- $R_5$, $R_6$, $R_7$ and $R_8$ are hydrogen or alkyl groups containing from 1 to 5 carbon atoms provided that only two of thse substituents may be a secondary or tertiary alkyl group.

2. Description of the Prior Art

Vinyl and vinylidene monomers useful in the preparation of polymeric materials and a variety of polymerizable compositions containing said monomers are well known in the art.

It is, of course, essential that any monomer-containing composition be stable when stored and that it not undergo premature polymerization during the time from preparation of the composition to that at which it is used. To accomplish this a variety of additives, generally referred to as polymerization inhibitors, have been suggested for inclusion in the composition. These have included, for example, t-butyl catechol, hydroquinone and derivatives thereof such as toluhydroquinone, mono-t-butylhydroquinone, 2,5-di-t-butylhydroquinone and hydroquinone monomethyl ether. However, these materials are often of limited solubility in the monomer employed, or are either volatile or thermally unstable at the elevated temperatures employed in the preparation of the polymerizable compositions in which they are used. To overcome these difficulties it is often necessary to employ mixtures of two or more inhibitors to produce the desired result. It would, therefore, be desirable to have a polymerization inhibitor which could be readily dissolved in the vinyl or vinylidene monomer containing composition at the concentration required to inhibit polymerization of the monomer and which would possess a high boiling point to minimize loss of the inhibitor from compositions which are prepared at elevated temperatures.

To be acceptable as a practically useful polymerization inhibitor, a material must satisfy at least two essential criteria. First, the material must be capable of preventing premature polymerization of the monomer-containing composition in which it is to be utilized. Secondly, when the material is incorporated in a composition which is intended to be polymerized when it is used, it is essential that the inhibitor used not adversely affect either the cure characteristics of the composition or the properties of the polymeric material prepared therefrom. As is well known to those skilled in the art, while there are a variety of materials which will satisfy the first of these criteria, the number of available additives which will satisfy the second criteria is much lower.

Many biphenols and derivatives thereof are known in the art and have been suggested for use in a variety of applications. Thus, U.S. Pat. Nos. 2,479,948 issued to Luten et al., 2,785,188 issued to Coe, and 3,631,208 issued to Hay, disclose that biphenols, including a variety of alkyl derivatives thereof, are useful as stabilizers to prevent oxidative degradation of a variety of materials including petroleum distillates such as cracked gasoline, lubricating oils and hydrocarbon polymers; animal oils; fish oils; synthetic cellulose derivatives; polymers of unsaturated materials; fats; oils; soaps; and aromatic amines. Also, in U.S. Pat. Nos. 3,720,721 and 3,748,303, both of which are issued to Becker et al., it is disclosed that some halogenated tetraalkyl biphenols can be used as antioxidants for petroleum products and as stabilizers against polymerization of monomeric materials to maintain them in the essentially unpolymerized state until such time as they are ready for polymerization.

Several additional references also disclose the use of various biphenols as antioxidants for organic compounds. See, in this regard, U.S. Pat. Nos. 3,153,098 and 3,251,801 both of which are issued to Boag; U.S. Pat. Nos. 3,247,262 issued to Kaeding; 3,383,395 issued to Schmukler; 3,562,338 issued to Zaweski; and 2,905,674 issued to Filbey.

It has now been discovered that certain biphenol derivatives are especially useful as polymerization inhibitors in compositions containing a vinyl or vinylidene monomer capable of free radical polymerization.

SUMMARY OF THE INVENTION

In accordance with the present invention it has been found that certain biphenol derivatives are particularly well suited for use as polymerization inhibitors in compositions containing a vinyl or vinylidene monomer capable of free radical polymerization. The particular biphenol derivatives which have been found to be useful for this purpose may be represented by the following general formula:

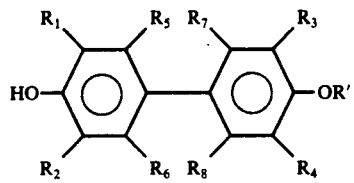

wherein
- R' is hydrogen or an alkyl group containing from 1 to 4 carbon atoms,
- $R_1$, $R_2$, $R_3$ and $R_4$ are alkyl groups containing from 1 to 5 carbon atoms, and
- $R_5$, $R_6$, $R_7$ and $R_8$ are hydrogen or alkyl groups containing from 1 to 5 carbon atoms provided that only two of these may be a secondary or tertiary alkyl group.

DESCRIPTION OF THE PREFERRED EMBODIMENTS

As mentioned above, the compositions of the present invention comprise a vinyl or vinylidene monomer and a biphenol derivative. Each of these components is discussed in detail below.

Biphenol Derivatives

As mentioned above, the biphenol derivatives useful as polymerization inhibitors in the compositions of the present invention are represented by the following general formula:

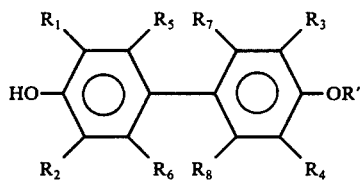

wherein
R' is hydrogen or an alkyl group containing from 1 to 4 carbon atoms,
$R_1$, $R_2$, $R_3$ and $R_4$ are alkyl groups containing from 1 to 5 carbon atoms, and
$R_5$, $R_6$, $R_7$ and $R_8$ are hydrogen or alkyl groups containing from 1 to 5 carbon atoms provided that only two of these may be a secondary or tertiary alkyl group.

In the compositions of the resent invention it is preferred to employ symmetrical biphenols — i.e., those in which the substituents ortho and meta to the biphenyl linkage are identical on both benzene rings. Thus, it is preferred that the substituents in the pairs $R_1$ and $R_3$; $R_2$ and $R_4$; $R_5$ and $R_7$; and $R_6$ and $R_8$ be the same.

Preferred materials are those in which $R_5$, $R_6$, $R_7$ and $R_8$ are all hydrogen. Representative materials having this formula which may be employed include, for example, the following:

3,3',5,5'-tetramethyl-4,4'-biphenol,
3,3',5,5'-tetramethyl-4,4'-biphenol monomethyl ether,
3,3'-dimethyl-5,5'di-t-butyl-4,4'-biphenol,
3,3',5,5'-tetra-sec-butyl-4,4'-biphenol,
3,3'5,5'-tetra-t-butyl-4,4'-biphenol,
3,3',5,5'-tetraisopropyl-4,4'-biphenol, and
3,3'-dimethyl-5,5'-diethyl-4,4'-biphenol.

Especially preferred results are achieved when either 3,3',5,5'-tetramethyl-4,4'-biphenol or 3,3'-dimethyl-5,5'-di-t-butyl-4,4'-biphenol is utilized as the polymerization inhibitor.

Other biphenol derivatives which may be utilized include, for example, 2,2',3,3',5,5'-hexamethyl-4,4'-biphenol,
2,2',3,3',5,5'-hexaethyl-4,4'-biphenol,
2,2'-diethyl-3,3',5,5'-tetramethyl-4,4'-biphenol,
2,2'3,3'-tetraethyl-5,5'-di-t-butyl-4,4'-biphenol,
2,2',3,3',5,5',6,6'-octamethyl-4,4'-biphenol,
2,2',3,3',6,6'-hexamethyl-5,5'-di-t-butyl-4,4'-biphenol,
2,2',3,3',5,5'-hexamethyl-6,6'-di-t-butyl-4,4'-biphenol,
2,2',3,3'-tetramethyl-5,5',6,6'-tetraethyl-4,4'-biphenol, and
2,2'-diethyl-3,3'-dimethyl-5,5'-di-isopropyl-6,6'-di-t-butyl-4,4'-biphenol.

These alkyl-substituted biphenols may be prepared by methods which are known in the art. Generally, these methods involve the oxidative coupling of an alkylphenol in the presence of a suitable catalyst in accordance with the following general reaction wherein R is hydrogen or alkyl as indicated above.

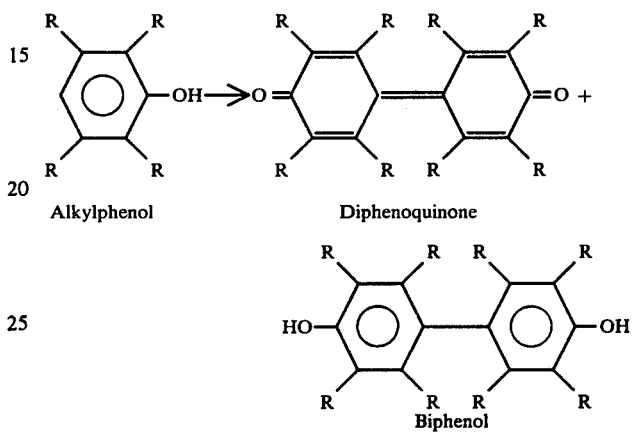

If the reaction results in the diphenoquinone, this material may be hydrogenated to the corresponding biphenol.

In one method, the biphenols may be prepared by the oxidative coupling of an alkylphenol using a combination of an alkaline material and a palladium catalyst as is described in U.S. Pat. No. 3,804,865 issued to Rutledge. The biphenols may also be prepared using a metal complex of an amino acid as is described in U.S. Application Ser. No. 500,210 entitled "Oxidative Coupling of Alkylphenols and Alkoxyphenols Catalyzed by Metal Complexes of Amino Carboxylic and Amino Sulfonic Acids" filed Aug. 23, 1974 by Rutledge (now abandoned), or by the use of a catalyst system comprising a copper compound, an anionic surfactant and an alkaline material as is disclosed in Application Ser. No. 499,826 entitled "Oxidative Coupling of Phenols" which was also filed Aug. 23, 1974 by Rutledge (now abandoned). The disclosure of these applications, both of which are assigned to the same assignee as the present application, is incorporated herein by reference.

In addition to the above, other methods known in the art may also be used to prepare the biphenols used in the compositions of the present invention.

The alkyl ethers of the biphenols may be prepared by reacting one of the above-mentioned biphenols with an alkyl halide such as methyl chloride, ethyl chloride, propyl chloride or t-butyl chloride in an aqueous medium and in the presence of an alkaline material such as sodium hydroxide.

The amount of the biphenol derivative employed in the stabilized compositions of the present invention may be varied depending upon the particular composition being stabilized and the time and conditions under which it must remain stable. Generally, an amount of biphenol derivative equal to up to about 0.3 percent by weight based upon the total weight of the polymerizable components in the composition is sufficient. At amounts in excess of this it has been found that the induction period — i.e., the time required for polymerization to begin when the composition is utilized, becomes longer than is desirable in most commercial applications. The minimum amount of biphenol derivative which may be utilized is not narrowly critical and any amount which will give some stabilization may be used. However, preferred results are achieved when at least 0.0005 percent by weight, based upon the total weight of the polymerizable components in the composition, of the biphenol derivative is added. Especially preferred results are achieved with an amount of biphenol derivative equal to from 0.001 to 0.1 percent by weight.

Monomer

In accordance with the present invention, there is also included in the composition a vinyl or vinylidene monomer capable of free radical polymerization. As used herein, the term "vinyl" refers to a monomer containing the monovalent radical $CH_2=CH-$ and "vinylidene" refers to a monomer containing the bivalent radical $CH_2=C<$.

Preferred compositions are those which contain a vinyl or vinylidene monomer which satisfies the following criteria:

a. liquid at room temperature,
b. capable of free radical polymerization to yield high polymer, and
c. capable of dissolving the biphenol derivative in the amounts indicated above.

As mentioned above, the vinyl or vinylidene monomers which may be stabilized against premature polymerization in accordance with the present invention must be capable of free radical polymerization to yield polymer. Thus, particularly in the case of vinylidene monomers, where both groups are larger than methyl, these monomers polymerize slowly, if at all, by free radical chemistry and are, therefore, not preferred for use in the compositions of the present invention.

As is well known to those skilled in the art, free radical polymerization refers to those polymerization reactions which take place through intermediates having an odd number of electrons and, consequently, an unpaired electron. It is these intermediates which are generally referred to as free radicals. The free radicals are normally generated in any one of a variety of ways such as by the decomposition of a chemical initiator added to the polymerizable mixture or by the application of heat or ionizing radiation to the composition. Suitable chemical initiators which may be utilized include, for example, benzoyl peroxide and azobisisobutyronitrile. If the free radical is generated in the presence of a vinyl or vinylidene monomer described above, the radical will add to the double bond with the regeneration of another radical. This radical will, in turn, react with another monomer and in the course of the reaction generate another free radical resulting in growth of the polymer chain through the addition of one chain to another. Free radical polymerization is described in detail in, for example, the *Encyclopedia of Polymer Science and Technology*, Vol. 7, pages 361–431, Interscience Publishers, 1967, and in the *Textbook of Polymer Science*, Billmeyer, Interscience Publishers, 1962, pages 262–290.

In addition to growth of the polymer chain, several side reactions can also take place during the course of the polymerization reaction. One of these, identified as chain transfer, refers to the transfer of an atom between the free radical and another molecule in the reaction mixture. Depending upon the nature of the other material, this can result in the formation of additional polymer molecules, the formation of branch chain polymers, or in termination of the polymerization reaction on a growing radical chain.

Chain transfer agents do not terminate the polymerization reaction entirely but merely terminate a growing chain and allow the polymerization to start elsewhere. If premature termination of the growing polymer chain occurs, a reduced molecular weight results and the desired polymer properties are not achieved. It is, for this reason, undesirable to include in a free radical polymerization system a polymerization inhibitor which would function in this manner. Similarly, it is undesirable to include a material which would retard the polymerization reaction.

As defined in the Billmeyer reference referred to above, a retarder is "a substance which can react with a radical to form products incapable of adding monomer." The addition of a material which would function as a retarder to a polymerizable composition could interfere with both the polymerization rate and the molecular weight of the resulting polymer. If the retarder is very effective no polymer will be formed and such a material is often referred to as an inhibitor. However, as was mentioned above, in systems such as those involved in the present invention, it is essential that the inhibitor prevent polymerization only until that time at which it is desired to polymerize the reaction mixture at which time the inhibitor must be eliminated and the reaction must then proceed with essentially the same characteristics as if the inhibitor had not been utilized. It is also essential that the polymerization inhibitor not react with the free radicals produced during the polymerization reaction to form a substance which is a retarder, thereby reducing the concentration of radicals and shortening their average life and thus the length of the polymer chain.

It has been found that the biphenol derivatives employed in the present invention do not act as either chain transfer agents or retarders during polymerization of the composition.

As mentioned above, any vinyl or vinylidene monomer capable of free radical polymerization may be utilized in the stabilized compositions of the present invention. Preferred monomers are those which are liquids at room temperature and in which the biphenol is soluble in the amounts indicated above. Especially preferred vinyl monomers are those selected from the group consisting of styrene, acrylic acid, methacrylic acid, alkyl esters of acrylic acid or methacrylic acid wherein the alkyl groups contain from 1 to 18 carbon atoms, acrylamide, methacrylamide, N-alkyl acrylamide wherein the alkyl groups contain from 1 to 18 carbon atoms, acrylonitrile, alpha substituted acrylonitrile such as alpha chloro-, alpha phenyl-, and alpha methylacrylonitrile and vinyl acetate.

Vinyl monomers which are solids at room temperature may also be utilized in the compositions of the present invention. When such a monomer is employed the biphenol derivative is dispersed or blended with said material. The blending operation may be conducted using apparatus and methods known in the art for forming intimate mixtures of two or more solid materials. Solutions of these normally solid vinyl monomers either in a liquid vinyl monomer in which they are soluble or in a suitable solvent may also be employed in the compositions of this invention.

In addition to compositions containing one of the vinyl or vinylidene monomers referred to above, it has also been found in accordance with the present invention that compositions containing an additional material capable of copolymerizing with the vinyl or vinylidene monomer may also be stabilized by the use of the biphenol derivatives defined above. These compositions include, in addition to the vinyl or vinylidene monomer, an additional ethylenically unsaturated material which is capable of cross-linking with the vinyl or vinylidene monomer to produce polymer. Representative of these additional materials are, polyester resins, particularly those prepared by the reaction of a polyhydric alcohol, such as ethylene glycol, propylene glycol, alkoxylated bisphenol A, or pentaerythritol with a dicarboxylic acid or a mixture of dicarboxylic acids at least the major proportion of which — i.e., at least about 50 percent by weight of the total weight of the dicarboxylic acid, is an ethylenically unsaturated acid. In the preparation of the polyester resins it will, of course, be appreciated by those skilled in the art that anhydrides of these acids may also be utilized. Other materials which may be included in the compositions include vinyl urethane resins, which are the reaction product of a polyhydric alcohol, an isocyanate having a functionality equal to at least about 2.0 and containing terminal ethylenic unsaturation introduced into the polymer molecule by including in the reaction mixture an ethylenically unsaturated monohydroxyl compound such as a hydroxyl terminated ester of acrylic or methacrylic acid including, for example, hydroxy ethyl methacrylate and hydroxy propyl methacrylate.

In the compositions stabilized in accordance with the present invention the amount of vinyl or vinylidene monomer is generally equal to at least about 30 percent by weight based on the total weight of the composition. Preferably, the amount of monomer is equal to at least about 50 percent by weight based on the total weight of the composition.

Preferred results have been achieved with compositions containing a vinyl monomer and an unsaturated polyester resin. Especially preferred results are achieved with a polyester resin derived from a polyhydric alcohol having the following general formula:

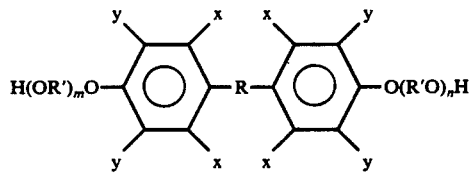

wherein
R is an alkylidene radical containing from 1 to 4 carbon atoms, a cycloalkylidene radical containing 5 or 6 carbon atoms, oxygen, sulfur or a divalent radical represented by the formula

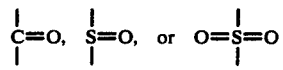

X is hydrogen, halogen, or a primary or secondary alkyl group containing from 1 to 4 carbon atoms; Y is hydrogen, halogen, or a primary, secondary or tertiary alkyl group contaning from 1 to 4 carbon atoms; provided that the total number of halogen substituents on each benzene ring is equal to 2 or less; R' is an alkylene group; and m and n are integers each of which is equal to at least 1 and the sum of which is equal to from 2 to about 16;

and a dicarboxylic acid or a mixture of dicarboxylic acids wherein at least 80 mol percent of said dicarboxylic acid is an ethylenically unsaturated acid such as fumaric acid or maleic acid.

If a vinyl urethane resin is employed in the composition, it is preferred to utilize one of the resins described in U.S. Patent Application Ser. No. 364,912 (now U.S. Pat. No. 3,876,726) entitled "Vinyl Ester Urethanes" and filed May 29, 1973. The disclosure of that application, which is assigned to the same assignee as the present application, is incorporated herein by reference. As described in said application, these vinyl urethane resins are the reaction product of (a) an ester prepared from a polyoxyalkylene bisphenol A and an unsaturated, aliphatic, dicarboxylic acid, (b) a diisocyanate and (c) a hydroxyl-terminated ester of acrylic or methacrylic acid, and may be represented by the following general formula:

$$R - A - M]_y A - I - B$$

wherein
A is a radical derived from a polyoxyalkalene bisphenol having the following formula:

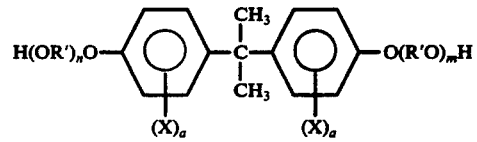

wherein
R' is an alkylene group,
X is halogen or methyl,
a is an integer equal to from 0 to 2, and
m and n are integers each of which is equal to at least 1 and the sum of which is equal to from about 2 to about 6;

M is a radical derived from an unsaturated, aliphatic, dicarboxylic acid or an anhydride thereof;
I is a radical derived from a diisocyanate,
B is a radical derived from a hydroxy-terminated ester of acrylic or methacrylic acid;
y is an integer equal to from 1 to about 5; and
R is selected from the group consisting of hydroxyl, I and I — B, wherein I and B are as defined above.

In order to describe the present invention so that it may be more clearly understood, the following examples are set forth. These examples are given primarily for the purpose of illustration and any enumeration of detail contained therein should not be interpreted as a limitation on the concept of the present invention.

In the examples, the following standard tests were employed:

Cure properties — i.e., gel time, gel to peak time, and peak temperature — were measured in accordance with the following procedure:

100 grams of the vinyl monomer composition and a catalyst were added to an 8-oz. jar and the mixture was stirred. The time interval between the addition of the catalyst and the point at which the free-flowing resin solution become stringy, as evidenced by the appearance of gelly-like masses, was recorded as "Gel Time". At this point, a thermocouple hooked to a recorder was inserted into the center of the composition to a point about ½ inch from the bottom of the jar. The interval between the gel time and the time at which the maximum exotherm temperature was reached is referred to as "Gel to Peak Time". The maximum exotherm temperature is referred to as "Peak Temperature".

In Example 18 viscosity was measured at 25° C. using a Brookfield viscometer, Model LVF with a number 3 spindle at 30 rpm.

In the remaining examples the viscosity was measured at the temperature to which the composition had been heated using Ostwald viscometers. The viscosities are reported as relative viscosity — i.e., the viscosity of the monomer — polymer solution/viscosity of pure monomer.

Examples 1 thru 6 illustrate the preparation of representative biphenol derivatives useful as polymerization inhibitors in the compositions of the present invention.

EXAMPLE 1

Preparation of 3,3',5,5'-tetramethyl-4,4'-biphenol

Into a 500 ml., creased Morton flask, fitted with a gas addition tube, a condenser, a thermometer and a stirrer capable of operating at speeds in the range of from about 8,000 to about 10,000 rpm., there were added
48.8 grams (400 mmoles) of 2,6-xylenol,
0.20 gram (0.6 mmoles) of sodium lauryl sulfate, and
150 ml of ion exchanged water.

The mixture was stirred under oxygen and heated to a temperature of 55° C. At that time a solution of 0.4 gram (2 mmoles) of cupric acetate monohydrate in 50 ml of water was added. There was then added dropwise, over a period of 1½ minutes, 8 ml of a 1.0 N- sodium bicarbonate solution.

The reaction mixture was heated to a temperature of 80° C. and a slow stream of oxygen was introduced. At the end of 6 hours, the reaction was flushed with nitrogen and cooled to a temperature of 20° C.

The reaction mixture was filtered through a medium porosity, sintered-glass funnel under slight vacuum. The recovered solid was washed with water and filtered again. A sample of the solid was removed and any unreacted 2,6-xylenol was determined by GLC analysis. The analysis indicated 8 mol percent of unreacted 2,6-xylenol.

The water-washed solid was air dried and washed twice with 150 ml of benzene to remove 2,6-xylenol and polyphenoxy ether. The resulting yellow solid was dried at 60° C. The yield of 3,3',5,5'-tetramethyl-4,4'-biphenol was equal to 80 mol percent.

EXAMPLE 2

Preparation of 3,3',5,5'-tetramethyl-4,4'-biphenol

Into a first flask there were added:
0.40 grams (2 mmols) of cupric acetate monohydrate,
0.30 grams (4 mmols) of glycine, and
50 ml of ion exchanged water.
Into a 500 ml creased Morton flask, fitted with a gas addition tube, a condenser, a thermometer, and a stirrer capable of operating at speeds in the range of from about 8,000 to about 10,000 rpm, there were added:
48.8 grams (400 mmols) of 2,6-xylenol, and 150 ml of ion exchanged water.

To the resulting slurry there was added the copper/glycine composition prepared above. The resulting mixture was stirred under oxygen and heated to a temperature of 50° C. There was then added 8.0 ml of a 1.0 Normal sodium bicarbonate solution.

The reaction mixture was heated to a temperature of 80° C. and a slow stream of oxygen was introduced. At the end of 6 hrs., the reaction was flushed with nitrogen and cooled to a temperature of 20° C.

The reaction mixture was filtered and the solids washed with water. A sample of the solid was removed, dissolved in acetone and analyzed by gas-liquid chromatography. The analysis indicated that 1 mol percent of the 2,6-xylenol was unreacted.

The dried solid weighing 43.8 grams was washed twice with 100 ml of benzene to remove 2,6-xylenol and polyphenoxy ether. The resulting solid was dried at 60° C. Analysis of the product indicated a yield of tetramethyl diphenoquinone equal to 28.6 mol percent. The yield of 3,3',5,5'-tetramethyl-4,4'-biphenol was calculated as 50.3 mol percent.

EXAMPLE 3

Preparation of 3,3',5,5'-tetramethyl-4,4'-biphenol

Into a 500 ml., creased Morton flask fitted with a gas addition tube, a condenser, a thermometer and a stirrer capable of operating at speeds in the range of from about 8,000 to about 10,000 rpm there was added:
48.8 grams of 2,6-xylenol dissolved in 125 ml of xylene.

There was then added 175 ml of water containing 0.1 ml of a 4.5 N solution of sodium hydroxide and 1.0 grams of a palladium-carbon catalyst containing 5 percent by weight palladium. The amount of alkaline material added was equal to 0.37 percent by weight and the amount of palladium was equal to 0.10 percent.

The reaction mixture was heated to a temperature of 40° C. and a slow stream of oxygen which had been purified by passing through sodium pellets, granular charcoal and concentrated sulfuric acid was introduced. After about 20 minutes, diphenoquinone began to form, as evidenced by the appearance of a red color in the reaction mixture. At the end of 6 hrs., all of the 2,6-xylenol had been reacted, as evidenced by GLC analysis of a sample removed from the reaction mixture. At this time, the reactor was flushed with nitrogen and cooled to a temperature of 20° C.

The reactor mixture was filtered through a medium porosity, sintered-glass funnel under slight vacuum to remove a purplish-red solid. The solid was washed twice with 25 ml portions of benzene and air dried. When dried, the solid was placed in a Soxhlet thimble and extracted with methylene chloride until the extract were a very pale yellow color. The methylene chloride was then removed, resulting in 31 grams of a solid product. The product was further purified by stirring with a mixture of methanol, water and sodium hydroxide filtering and washing the solid with water until the pH of the filtrate was approximately neutral. There resulted 30 grams of tetramethyl diphenoquinone.

The purified tetramethyl diphenoquinone is converted to 3,3',5,5'-tetramethyl-4,4'-biphenol by slurrying the solid in methanol in the presence of a Raney nickel hydrogenation catalyst and introducing hydrogen while maintaining the temperature of the mixture a 60° C. until the reddish color of the diphenoquinone disappears.

EXAMPLE 4

Preparation of 3,3'-dimethyl,5,5'-di-t-butyl-4,4'-biphenol

Into a 500 ml, creased Morton flask, fitted with a gas addition tube, a condenser, thermometer, and a stirrer capable of operating at speeds in the range of from about 8,000 to about 10,000 rpm, there were added:

74.2 grams (452 mmoles) of 2-methyl-6-t-butylphenol,
0.2 gram (0.6 mmoles) of sodium lauryl sulfate, and
160 ml ion exchanged water.

The mixture was stirred and 40 ml water containing 0.4 gram (2 mmoles) cupric acetate monohydrate and 0.3 gram glycine (4 mmoles) were added. There were then added, over a period of 1½ minutes, 20 ml of 1.0 N-sodium bicarbonate solution.

The reaction mixture was heated to a temperature of 80° C. and a slow stream of oxygen was introduced. At the end of 6 hours, the reaction mixture was cooled to a temperature of 20° C. and acidified by adding 10 ml glacial acetic acid.

The reaction mixture was filtered and the solids washed with water. A sample of the solid was removed, dissolved in acetone, and analyzed by gas-liquid chromatography. The analysis indicated that 1.5 mole percent of the 2-methyl-6-t-butylphenol was unreacted.

The dimethyl-di-t-butyldiphenoquinone was converted to the biphenol by slurrying in methanol and introducing hydrogen in the presence of a palladium on carbon catalyst while maintaining the temperature of the mixture at about 65° C. until a clear solution results. The catalyst was filtered off and the filtrate poured into water to precipitate the solid product. The product was filtered off and dried.

EXAMPLE 5

Preparation of 3,3',5,5'-tetra-sec-butyl-4,4'-biphenol

Into a 500 ml, creased Morton flask, fitted with a gas addition tube, condenser, thermometer, and a stirrer capable of operating at speeds in the range of from about 8,000 to about 10,000 rpm, there were added:

123.8 grams (600 mmoles) of 2,6-di-sec-butylphenol,
0.20 gram (0.6 mmoles) of sodium lauryl sulfate, and
115 ml of ion exchanged water.

The mixture was stirred and 40 ml water containing 0.4 gram (2 mmoles) of cupric acetate monohydrate and 0.3 gram glycine (4 mmoles) were added. There were then added, over a period of 1½ minutes, 24 ml of 1.0 N-sodium bicarbonate solution.

The reaction mixture was heated to a temperature of 80° C. and a slow stream of oxygen was introduced. At the end of 6 hours, the reaction was cooled to a temperature of 20° C. and acidified with 10 ml of glacial acetic acid.

The reaction mixture was filtered through a medium porosity, sintered-glass funnel under slight vacuum. The recovered solid was washed with water and filtered again. GLC analysis of a sample indicated no unreacted 2,6-di-sec-butylphenol. The yield of air dried product was about 100 mol percent.

The tetra-sec-butyl diphenoquinone was converted to the tetra-sec-butylbiphenol by slurrying the solid in methanol in the presence of a palladium on carbon catalyst and introducing hydrogen to a pressure of 300 psi, while maintaining the temperature at about 100° C. for 4 hours. The resulting clear solution was filtered and the filtrate poured into water to precipitate the solid product. The product was filtered off and dried.

EXAMPLE 6

Preparation of 3,3',5,5'-tetramethyl-4,4'-biphenol monomethyl ether

Into a 4-liter autoclave there were placed 425 grams of (1.75 moles) of 3,3',5,5'-tetramethyl-4,4'-biphenol and 900 ml of distilled water having dissolved therein 77 grams (1.93 moles) of sodium hydroxide. The autoclave was sealed and shaken while being heated to 90° C. Over a 3 hour period there were added 97 grams (1.97 moles) of methyl chloride. When the addition was completed, the autoclave was heated to 168° C. and maintained at that temperature for 3 hours at the end of which time it was cooled to room temperature.

The contents were poured into 2 liters of toluene, the mixture stirred vigorously for 10 minutes, and the toluene layer separated. Evaporation of the toluene yielded 130 grams of the crude tetramethylbiphenol monomethyl ether. The material was purified by recrystallization from cyclohexane.

EXAMPLE 7

A composition was prepared comprising
100 grams of styrene, and
0.01 grams (.01 percent by weight) 3,3'-dimethyl-5,5'-di-t-butyl-4,4'-biphenol.

The composition was heated to 100° C. and the viscosity measured at various intervals over a period of 4 hours. As polymerization occurs the viscosity increases. The results are given in the following table and are compared with those obtained with a sample of styrene containing no inhibitor.

| TIME | RELATIVE VISCOSITY | |
|---|---|---|
| (Minutes) | .01% Inhibitor | No Inhibitor |
| 0 | 1.0 | 1.0 |
| 15 | 1.0 | 2.2 |
| 30 | 1.1 | 5.3 |
| 60 | 3.3 | 13.7 |
| 120 | 19.6 | 42.1 |
| 240 | 46.4 | — |

EXAMPLE 8

A composition was prepared comprising:
100 grams of styrene, and
0.01 gram (.01 percent by weight) 3,3',5,5'-tetra-sec-butyl-4,4'-biphenol.

The composition was heated to 100° C. and the viscosity measured at various intervals over a period of 4 hours. As polymerization occurs the viscosity increases. The results are given in the following table and are compared with those obtained with a sample of styrene containing no inhibitor.

| TIME | RELATIVE VISCOSITY | |
|---|---|---|
| (Minutes) | .01% Inhibitor | No Inhibitor |
| 0 | 1.0 | 1.0 |
| 15 | 1.3 | 2.2 |
| 30 | 2.1 | 5.3 |
| 60 | 5.4 | 13.7 |
| 120 | 34.1 | 42.1 |
| 240 | 70.4 | — |

EXAMPLE 9

A composition was prepared comprising:
100 grams of styrene, and
0.01 gram (.01 percent by weight) 3,3',5,5'-tetramethyl-4,4'-biphenol monomethyl ether.

The composition was heated to 100° C. and the viscosity measured at various intervals over a period of 2 hours. As polymerization occurs the viscosity increases. The results are given in the following table and are compared with those obtained with a sample of styrene containing no inhibitor.

| TIME | RELATIVE VISCOSITY | |
|---|---|---|
| (Minutes) | .01% Inhibitor | No Inhibitor |
| 0 | 1 | 1 |
| 15 | 1.17 | 2.52 |
| 30 | 3.34 | 6.10 |
| 60 | 9.77 | 17.4 |
| 120 | 33.3 | 44.8 |

EXAMPLES 10–13

Into a 2-liter, three necked flask, equipped with a stirrer, nitrogen inlet tube, thermometer and a horizontal condenser to collect water resulting from the esterification reaction, there were added:
1220 grams (3.45 moles) of polyoxypropylene(2.2-)bis4-hydroxyphenyl)2,2-propane (the reaction product of 2.2 moles of propylene oxide and 1 mole of bisphenol A), and
338 grams (3.45 moles) of maleic anhydride.

The resulting mixture was stirred and heated to a temperature of from 210° C. to 215° C. over a period of 1 hour. The reaction mixture was maintained at this temperature for 5 hours, at the end of which time vacuum (28 mm) was applied and held for 1 hour. There was then added 0.78 grams (0.05 percent by weight based on the weight of the reaction mixture) of 3,3',5,5'-tetramethyl-4,4'-biphenol. The resulting mixture was held at 215° C. for 1 hour at the end of which time it was removed from the reaction flask. The resulting polyester had a melting point of 97° C., an acid number of 15.4, a saponification number of 241 and a hydroxyl number of 46.7.

A composition was prepared containing:
50 grams of the polyester resin prepared above, and
50 grams of styrene.

The resulting composition was a clear, amber colored solution. To the resulting composition there was added a catalyst mixture containing:
1.0 gram of a 60 percent by weight solution of methyl ethyl ketone peroxide and dimethyl phthalate,
1.0 gram of cobalt naphthanate, and
0.2 gram of dimethylaniline.

This composition had the following cure properties:

Gel Time — 7 minutes
Gel to Peak Time — 7 minutes
Peak Temperature — 196° C.

By comparison, a control sample which did not contain any of the biphenol derivative had the following cure properties when treated in exactly the same manner:

Gel Time — 4 minutes
Gel to Peak Time — 6 minutes
Peak Temperature — 197° C.

The longer gel time in the composition containing the biphenol derivative shows that this material is an effective polymerization inhibitor in this composition.

Employing the same procedures described above, three additional compositions were prepared containing varying amounts of the biphenol derivative. The amounts of tetramethyl biphenol employed, the properties of the resulting polyester resin and the cure properties of compositions containing this resin are given in the following tables.

TABLE I

| | Tetramethylbiphenol | | Polyester Resin | | | |
|---|---|---|---|---|---|---|
| | | | Melting Point | Acid | Saponification | Hydroxyl |
| Ex. | grams | percent | (° C) | Number | Number | Number |
| 11 | 1.56 | 0.10 | 95 | 13.5 | 224 | 51 |
| 12 | 2.34 | 0.15 | 94 | 13.9 | 239 | 51.5 |
| 13 | 3.12 | 0.20 | 95 | 14.2 | 238 | 55.8 |

TABLE II

| | CURE PROPERTIES | | |
|---|---|---|---|
| Example | Gel Time (minutes) | Gel to Peak Time (minutes) | Peak Temperature (° C) |
| Control | 4 | 6 | 197 |
| 11 | 17 | 4 | 188 |
| 12 | 37 | 12 | 183 |
| 13 | 54 | 15 | 174 |

EXAMPLE 14

Into a 2-liter, three necked reaction flask, equipped with a stirrer, nitrogen inlet tube, thermometer and a horizontal condenser tube to collect the water of esterification, there were added:
1220 grams (3.45 moles) of polyoxypropylene(2.2)-bis(4-hydroxyphenyl)propane,
338 grams (3.45 moles) of maleic anhydride, and
1.56 grams (0.10 percent by weight) of 3,3',5,5'-tetramethyl-4,4'-biphenol.

The resulting reaction mixture was heated to a temperature of from 210° to 215° C. over a period of 1 hour and maintained at that temperature for a period of 5 hours. At the end of this time, vacuum (28 mm) applied and held for one hour. The entire reaction mixture was then held at a temperature of 215° C. for an additional hour. At the end of this time the polyester resin was removed from the reaction flask. This resin had a melting point of 95° C., an acid number of 13.6, a saponification number of 244 and a hydroxyl number of 46.8.

A composition was prepared by dissolving 50 grams of the resin in 50 grams of styrene. To this composition there was then added the catalyst system described in Example 10. When cured, this composition had the following properties:

Gel Time — 16 minutes
Gel to Peak Time — 6 minutes
Peak Temperature — 188° C.

EXAMPLES 15–16

Employing the procedure described in Example 14, varying amounts of tetramethylbiphenol were added to the polyester resin. The amounts of tetramethylbiphenol employed, the properties of the resulting resin and the cure properties of styrene compositions containing the polyesters are given in the following tables.

TABLE III

| Ex. | Tetramethyl-biphenol grams | Tetramethyl-biphenol percent | Melting Point (° C) | Acid Number | Saponification Number | Hydroxyl Number |
|---|---|---|---|---|---|---|
| 15 | 2.12 | 0.136 | 96 | 14.4 | 240 | 52 |
| 16 | 2.34 | 0.15 | 95 | 14.4 | 238 | 51 |

TABLE IV

| | CURE PROPERTIES | | |
|---|---|---|---|
| Example | Gel Time (minutes) | Gel to Peak Time (minutes) | Peak Temperature (° C) |
| 15 | 31 | 10 | 184 |
| 16 | 33 | 10 | 184 |

EXAMPLE 17

A polyester resin was prepared as described in Example 10 except that no biphenol derivative was added during the reaction. Into each of eight bottles, there were added:
200 grams of the polyester resin, and
200 grams of styrene.

Into four of these bottles, varying amounts of 3,3′,5,5′-tetramethyl-4,4′-biphenol were added. The bottles were closed and rolled on a roller bar for 24 hours to dissolve the biphenol derivative. To each of these bottles there was then added a catalyst composition containing 4.0 grams of a 60 percent by weight solution of methyl ethyl ketone peroxide in dimethylphthalate, 4.0 grams of cobalt naphthanate, and 0.8 gram of dimethylaniline.

Cure properties of the resulting compositions were determined as in Example 10. The amounts of tetramethylbiphenol employed and the cure properties are given in the following table. The percent of biphenol derivative is given as percent by weight based upon the total weight of the composition — i.e., polyester resin plus styrene.

TABLE V

| | Cure Properties | | |
|---|---|---|---|
| Tetramethylbiphenol (% by weight) | Gel Time (minutes) | Gel to Peak Time (minutes) | Peak Temperature (° C) |
| .025 | 7 | 7 | 196 |
| .050 | 17 | 4 | 188 |
| .075 | 37 | 12 | 183 |
| .100 | 54 | 15 | 174 |

Into the remaining four bottles, there were added varying amounts of 2-chloro-3,3′,5,5′-tetramethyl-4,4′-biphenol prepared as described in U.S. Patent Application Ser. No. 311,496 (now U.S. Pat. 3,894,094), entitled "Halogenated Tetraalkyl Biphenols" filed Dec. 4, 1972 and assigned to the same assignee as the present application. These samples were also rolled as described above and the catalyst composition described above was added to each of them. The amounts of chlorinated tetramethylbiphenol and the cure properties of the resulting compositions are given in the following table. Here also, the amounts of chlorinated tetramethylbiphenol are given in terms of percent by weight based upon the total weight of the styrene and polyester in the composition.

TABLE VI

| | Cure Properties | | |
|---|---|---|---|
| Chloro-tetramethylbiphenol (% by weight) | Gel Time (minutes) | Gel to Peak Time (minutes) | Peak Temperature (° C) |
| .025 | 2 | 6 | 196 |
| .050 | 8 | 7 | 198 |
| .075 | 15 | 8 | 194 |
| .100 | 30 | 13 | 186 |

EXAMPLE 18

Into a 1-liter resin kettle, equipped with a stirrer, thermometer, nitrogen inlet tube and a condenser for collecting water, there were added:
768 grams (2.2 moles) of polyoxypropylene(2.2)-bis(4-hydroxyphenol)propane, and
215 grams (2.2 moles) of maleic anhydride.

The resulting mixture was heated to a temperature of 220° C. and maintained at that temperature for 2 hours. During this time water produced during the course of the reaction was removed by distillation. The total amount of water removed was equal to 28 ml. At the end of this time, there was added 0.19 gram (.02 percent by weight based upon the weight of the polyester) of 3,3′,5,5′-tetramethyl-4,4′-biphenol. The heat was reduced to a temperature of from 190° C. to 195° C. and maintained at that temperature for 60 minutes. At the end of this time the resin was removed from the kettle.

A composition was prepared by combining 50 grams of the resin prepared above and 50 grams of styrene. This resulted in a clear, amber colored solution having a viscosity of 544. The resin solution was aged at 60° C. and the viscosity measured weekly on a sample which was removed and cooled to 25° C. before measuring viscosity. The results are given in the table below.

As a control, an identical resin was prepared containing 0.02 percent by weight of hydroquinone, a conventional stabilizer employed in compositions such as this. This material was also stored at 60° C. and the viscosity measured weekly on samples which had been cooled to 25° C. This data is also given in the table below.

TABLE VII

| Time (weeks) | Viscosity (centipoise) | |
|---|---|---|
| | Biphenol Derivative | Hydroquinone |
| 0 | 544 | 576 |
| 1 | 640 | 736 |
| 2 | 880 | 1024 |
| 3 | 1216 | 1696 |
| 4 | 1760 | 2560 |
| 5 | 2800 | 4368 |
| 6 | 4500 | gelled |
| 7 | gelled | — |

EXAMPLE 19

A composition was prepared comprising:
100 grams of styrene, and
0.01 gram (.01 percent by weight) of 3,3′,5,5′-tetramethyl-4,4′-biphenol.

The composition was heated to 100° C. and the viscosity measured at various intervals over a period of 2 hours. As polymerization occurs the viscosity increases. The results are given in the following table and are compared with those obtained with a sample of styrene containing no inhibitor.

| TIME (Minutes) | RELATIVE VISCOSITY | |
|---|---|---|
| | .01% Inhibitor | No Inhibitor |
| 0 | 1 | 1 |
| 15 | 1.19 | 2.4 |
| 30 | 2.43 | 4.41 |
| 60 | 5.37 | 11.3 |
| 120 | 18.80 | 37.8 |

EXAMPLE 20

A composition was prepared comprising:
100 grams of methyl methacrylate, and
0.00156 gram of 3,3′,5,5′-tetramethyl-4,4′-biphenol.

The composition was heated to 100° C. and the viscosity measured at various intervals over a period of 2 hours. As polymerization occurs the viscosity increases. The results are given in the following table and are compared with those obtained with a sample of methyl methacrylate containing no inhibitor.

| TIME | RELATIVE VISCOSITY | |
|---|---|---|
| (Minutes) | .01% Inhibitor | No Inhibitor |
| 0 | 1 | 1 |
| 60 | 1 | 167.9 |
| 120 | 1 | — |

EXAMPLE 21

A composition was prepared comprising:
100 grams of vinyl acetate,
0.004 gram of benzoyl peroxide, and
0.005 gram of 3,3',5,5'-tetramethyl-4,4'-biphenol.

The composition was heated to 70° C. and the viscosity measured at various intervals over a period of 2 hours. The results are given in the following table and are compared with those obtained with a sample of vinyl acetate and the same amount of benzoyl peroxide but without any inhibitor.

| TIME | RELATIVE VISCOSITY | |
|---|---|---|
| (Minutes) | .01% Inhibitor | No Inhibitor |
| 0 | 1 | 1 |
| 30 | 1.03 | 2.1 |
| 60 | 1.21 | 12.8 |
| 120 | 1.38 | — |

EXAMPLE 22

Into a two-liter reaction flask equipped with a stirrer, thermometer, nitrogen inlet tube, and distillation head, there were added 1,416 (4 moles) of polyoxypropylene bisphenol A — i.e., the reaction product of 2.2 moles of propylene oxide per mole of bisphenol A, and 196 grams (2 moles) of maleic anhydride. The resulting reaction mixture was heated to from 210° C. to 215° C. and held at that temperature for 5 hours. At this time, the acid number had dropped to 11.7. Vacuum was then applied to the reaction mixture for 1 hour while maintaining the temperature at from 210° C. to 215° C. The vacuum was removed and the product was poured from the reaction flask. After cooling to room temperature, the product, identified as the diester of the polyoxypropylene bisphenol A, was an amber semisolid having an acid number of 8.9, a saponification number of 142, and a hydroxyl number of 145.

Into a suitable reaction vessel, there were added 788 grams (1.0 mole) of the diester prepared above and 1.58 grams (0.2 percent by weight) of 3,3',5,5'-tetramethyl-4,4'-biphenol. The resulting mixture was heated to 80° C. and 300 grams (2.0 moles) of toluene diisocyanate was added over a period of 1 hour. When the addition was completed, the temperature of the reaction mixture had increased to 135° C. The reaction mixture was held at this temperature for an additional ½ hour and the molten resin removed from the reaction vessel. The resulting light-colored solid had a melting point of 97° C., an acid number of 7.6, a saponification number of 201, a hydroxyl number of 22, and no residual isocyanate.

The resulting resin is ground to a fine powder and dissolved at 50 percent by weight in styrene. The amount of biphenol inhibitor in this composition is thus equal to 0.1 percent by weight based upon the total weight of polymerizable components in the composition. The resulting composition is stable and does not undergo premature polymerization when stored.

EXAMPLE 23

A composition was prepared comprising:
100 grams of styrene, and
0.01 gram (.01 percent by weight) of 3,3',5,5'-tetramethyl-4,4'-biphenol (TMBP).

The composition was heated to 100° C. and the viscosity measured at various intervals over a period of 2 hours. As polymerization occurs the viscosity increases. The results are given in the following table and are compared with those obtained with a sample of styrene containing no inhibitor and a composition comprising
100 grams of styrene, and
0.01 gram (.01 percent by weight) of 2-chloro-3,3',5,5'-tetramethyl-4,4'-biphenol (Cl-TMBP) prepared as in Example 17.

| TIME | RELATIVE VISCOSITY | | |
|---|---|---|---|
| (Minutes) | TMBP | Cl-TMBP | No Additive |
| 0 | 1.00 | 1.00 | |
| 15 | 1.01 | 1.85 | |
| 30 | 1.54 | 3.33 | |
| 60 | 4.02 | 10.40 | |
| 120 | 23.30 | 39.40 | |

What is claimed is:

1. A polymerizable composition stabilized against premature polymerization comprising
    a. at least about 30 percent by weight based on the total weight of the composition of a vinyl or vinylidene monomer capable of free radical polymerization, and
    b. a polymerization inhibitor having the following general formula

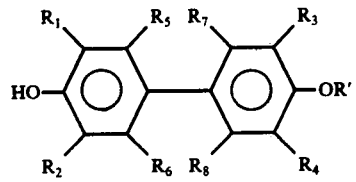

wherein
    R' is hydrogen or an alkyl group containing from 1 to 4 carbon atoms,
    $R_1$, $R_2$, $R_3$ and $R_4$ are alkyl groups containing from 1 to 5 carbon atoms, and
    $R_5$, $R_6$, $R_7$ and $R_8$ are hydrogen or alkyl groups containing from 1 to 5 carbon atoms provided that only two of these may be a secondary or a tertiary alkyl group.

2. A composition, as claimed in claim 1, wherein the vinyl monomer is a liquid at room temperature.

3. A composition, as claimed in claim 1, wherein the monomer is styrene.

4. A composition, as claimed in claim 1, wherein in the polymerization inhibitor R', $R_5$, $R_6$, $R_7$ and $R_8$ are hydrogen and $R_1$, $R_2$, $R_3$ and $R_4$ are alkyl groups.

5. A composition, as claimed in claim 4, wherein the alkyl groups are methyl.

6. A composition, as claimed in claim 4, wherein the alkyl groups are secondary butyl.

7. A composition, as claimed in claim 4, wherein $R_1$, and $R_3$ are methyl; and $R_2$ and $R_4$ are tertiary butyl.

8. A composition, as claimed in claim 1, wherein the amount of polymerization inhibitor is equal to up to about 0.3 percent by weight based upon the total weight of polymerizable components in the composition.

9. A composition, as claimed in claim 1, wherein the amount of polymerization inhibitor is equal to from about 0.01 to 0.1 percent by weight based upon the total weight of polymerizable components in the composition.

* * * * *

UNITED STATES PATENT AND TRADEMARK OFFICE
CERTIFICATE OF CORRECTION

PATENT NO. : 4,049,731
DATED : September 20, 1977
INVENTOR(S) : Alfred Joseph Restaino It is certified that error appears in the above-identified patent and that said Letters Patent are hereby corrected as shown below:

Column 3, line 35, "resent" should read -- present --.
Column 5, line 23, "$CH_2 = C<$." should read -- $CH_2 = C$ . --.

Column 8, line 29, "$R - A - M]_y A - I - B$" should read
-- $R \{A - M\}_y A - I - B$ --.

Column 9, line 5, "become" should read -- became --.
Column 13, line 29, ")bis4-hydroxyphenyl)2,2-propane" should read
-- )bis(4-hydroxyphenyl)2,2-propane --.
Column 14, TABLE I, line 6, column 6, "224" should read
-- 244 --.

Signed and Sealed this

*Fifteenth* Day of *May 1979*

[SEAL]

Attest:

RUTH C. MASON
*Attesting Officer*

DONALD W. BANNER
*Commissioner of Patents and Trademarks*